US009289279B2

(12) United States Patent
Wilson et al.

(10) Patent No.: US 9,289,279 B2
(45) Date of Patent: Mar. 22, 2016

(54) APPARATUS AND METHOD FOR LIMITING SURGICAL ADHESIONS

(75) Inventors: Jeffrey A. Wilson, Wrentham, MA (US); Michael Milbocker, Holliston, MA (US)

(73) Assignee: PROMETHEAN SURGICAL DEVICES, LLC, East Hartford, CT (US)

( * ) Notice: Subject to any disclaimer, the term of this patent is extended or adjusted under 35 U.S.C. 154(b) by 487 days.

(21) Appl. No.: 11/863,222

(22) Filed: Sep. 27, 2007

(65) Prior Publication Data

US 2008/0086216 A1    Apr. 10, 2008

Related U.S. Application Data

(60) Provisional application No. 60/850,239, filed on Oct. 6, 2006.

(51) Int. Cl.
*A61B 19/00* (2006.01)
*A61F 2/00* (2006.01)
*A61L 31/12* (2006.01)

(52) U.S. Cl.
CPC ............. *A61F 2/0063* (2013.01); *A61L 31/129* (2013.01); *A61B 2019/4884* (2013.01)

(58) Field of Classification Search
CPC .... C08G 18/10; C08G 18/12; C08G 18/4812; C08G 18/6677; C08G 18/755; C08G 2210/00; A61B 2019/4878; A61B 2019/4884; A61L 31/129; A61L 24/00; A61F 2/0063; A61F 2/0077
USPC ................................. 606/151–156, 213–215; 623/23.72–23.75; 523/105, 113; 424/422, 423, 443–445; 602/44, 52, 58
See application file for complete search history.

(56) References Cited

U.S. PATENT DOCUMENTS

| 3,054,406 | A | | 9/1962 | Usher |
|---|---|---|---|---|
| 3,124,136 | A | | 3/1964 | Usher |
| 3,769,071 | A | * | 10/1973 | Trancik ..................... 424/448 |
| 4,049,592 | A | | 9/1977 | Marans et al. |
| 4,193,137 | A | | 3/1980 | Heck |
| 4,347,847 | A | | 9/1982 | Usher |
| 4,352,264 | A | | 10/1982 | Seragnoli |
| 4,373,009 | A | | 2/1983 | Winn |
| 4,452,245 | A | | 6/1984 | Usher |
| 4,459,317 | A | | 7/1984 | Lambert |
| 4,487,808 | A | | 12/1984 | Lambert |
| 4,520,821 | A | | 6/1985 | Schmidt et al. |
| 4,577,631 | A | | 3/1986 | Kreamer |
| 4,633,873 | A | | 1/1987 | Dumican et al. |
| 4,655,221 | A | | 4/1987 | Devereux |

(Continued)

FOREIGN PATENT DOCUMENTS

EP            0334046 B1    6/1997

*Primary Examiner* — Dianne Dornbusch
(74) *Attorney, Agent, or Firm* — Mannava & Kang, P.C.

(57) ABSTRACT

A composite prosthesis and method for limiting the incidence of postoperative adhesions. The composite includes a non-inflammatory or coated mesh and a barrier material which prevents exposure of tissue elsewhere in the body to tissue covered by the composite prosthesis. The barrier material is absorbable which allows tissue through-growth and localization of the composite prosthetic. In use, the composite prosthesis is positioned over the tissue defect and may be positioned with the barrier material oriented against the tissue defect or repair site.

23 Claims, 8 Drawing Sheets

(56) References Cited

U.S. PATENT DOCUMENTS

| | | | |
|---|---|---|---|
| RE32,770 E | 10/1988 | Kaplan | |
| 4,804,691 A | 2/1989 | English et al. | |
| 4,838,267 A | 6/1989 | Jamiolkowski et al. | |
| 4,838,884 A | 6/1989 | Dumican et al. | |
| 4,840,626 A | 6/1989 | Linsky | |
| 4,990,357 A | 2/1991 | Karakelle | |
| 5,002,551 A | 3/1991 | Linsky | |
| 5,077,352 A | 12/1991 | Elton | |
| 5,156,613 A | 10/1992 | Sawyer | |
| 5,179,174 A | 1/1993 | Elton | |
| 5,209,776 A | 5/1993 | Bass et al. | |
| 5,410,016 A | 4/1995 | Hubbell | |
| 5,445,597 A | 8/1995 | Clark et al. | |
| 5,455,597 A | 10/1995 | Nakamura et al. | |
| 5,487,897 A | 1/1996 | Polson et al. | |
| 5,508,036 A | 4/1996 | Bakker | |
| 5,571,117 A | 11/1996 | Ahn | |
| 5,578,662 A * | 11/1996 | Bennett et al. | 524/54 |
| 5,593,441 A * | 1/1997 | Lichtenstein et al. | 600/37 |
| 5,634,931 A | 6/1997 | Kugel | |
| 5,645,931 A * | 7/1997 | Fan et al. | 428/334 |
| 5,665,106 A | 9/1997 | Hammerslag | |
| 5,795,584 A * | 8/1998 | Totakura et al. | 424/426 |
| 5,813,975 A | 9/1998 | Valenti | |
| 5,972,007 A | 10/1999 | Sheffield et al. | |
| 6,042,534 A | 3/2000 | Gellman et al. | |
| 6,077,216 A | 6/2000 | Benderev et al. | |
| 6,110,101 A | 8/2000 | Tihon et al. | |
| 6,123,667 A | 9/2000 | Poff et al. | |
| 6,191,216 B1 | 2/2001 | Ganster et al. | |
| 6,197,036 B1 | 3/2001 | Tripp et al. | |
| 6,211,335 B1 | 4/2001 | Owen et al. | |
| 6,221,005 B1 | 4/2001 | Bruckner et al. | |
| 6,258,124 B1 * | 7/2001 | Darois et al. | 623/14.13 |
| 6,265,016 B1 | 7/2001 | Hostettler et al. | |
| 6,296,607 B1 | 10/2001 | Milbocker | |
| 6,322,492 B1 | 11/2001 | Kovac | |
| 6,334,446 B1 | 1/2002 | Beyar | |
| 6,382,214 B1 | 5/2002 | Raz et al. | |
| 6,451,032 B1 * | 9/2002 | Ory et al. | 606/151 |
| 6,502,578 B2 | 1/2003 | Raz et al. | |
| 6,503,190 B1 | 1/2003 | Ulmsten et al. | |
| 6,524,327 B1 | 2/2003 | Spacek | |
| 6,589,269 B2 | 7/2003 | Zhu et al. | |
| 6,610,006 B1 | 8/2003 | Amid et al. | |
| 6,645,137 B2 | 11/2003 | Ulmsten et al. | |
| 6,652,595 B1 | 11/2003 | Nicolo | |
| 6,702,731 B2 | 3/2004 | Milbocker | |
| 6,736,823 B2 * | 5/2004 | Darois et al. | 606/151 |
| 6,736,854 B2 * | 5/2004 | Vadurro et al. | 623/23.72 |
| 6,749,554 B1 * | 6/2004 | Snow et al. | 600/3 |
| 7,011,688 B2 * | 3/2006 | Gryska et al. | 623/23.72 |
| 7,044,982 B2 * | 5/2006 | Milbocker | 623/23.72 |
| 7,439,062 B2 * | 10/2008 | Bhatt et al. | 435/325 |
| 7,504,386 B2 * | 3/2009 | Pressato et al. | 514/54 |
| 7,595,157 B2 * | 9/2009 | Tsinberg | 435/6.11 |
| 7,632,294 B2 * | 12/2009 | Milbodker et al. | 606/279 |
| 8,501,165 B2 * | 8/2013 | Molbocker | 424/78.17 |
| 2002/0012786 A1 * | 1/2002 | Iwasa et al. | 428/317.9 |
| 2002/0028980 A1 | 3/2002 | Thierfelder et al. | |
| 2002/0049503 A1 * | 4/2002 | Milbocker | 623/23.72 |
| 2003/0077328 A1 * | 4/2003 | Reeve et al. | 424/486 |
| 2003/0135238 A1 * | 7/2003 | Milbocker | 606/231 |
| 2004/0030380 A1 * | 2/2004 | Shulze et al. | 623/1.42 |
| 2004/0037866 A1 * | 2/2004 | Semertzides et al. | 424/423 |
| 2004/0068078 A1 | 4/2004 | Milbocker | |
| 2005/0070913 A1 * | 3/2005 | Milbocker et al. | 606/92 |
| 2005/0085924 A1 * | 4/2005 | Darois et al. | 623/23.74 |
| 2005/0129733 A1 * | 6/2005 | Milbocker et al. | 424/423 |
| 2005/0215748 A1 | 9/2005 | Milbocker | |
| 2005/0283256 A1 | 12/2005 | Sommerich | |
| 2006/0067976 A1 * | 3/2006 | Ferraro et al. | 424/426 |
| 2006/0078586 A1 * | 4/2006 | Ferraro et al. | 424/423 |
| 2006/0141045 A1 * | 6/2006 | Bhatt et al. | 424/489 |
| 2006/0233852 A1 * | 10/2006 | Milbocker | 424/422 |
| 2008/0127859 A1 * | 6/2008 | Kolberg et al. | 106/285 |
| 2008/0138615 A1 * | 6/2008 | Kolberg et al. | 428/341 |
| 2009/0280153 A1 * | 11/2009 | Hunter et al. | 424/423 |
| 2010/0185219 A1 | 7/2010 | Gertzman et al. | |

* cited by examiner

APPARATUS AND METHOD FOR LIMITING SURGICAL ADHESIONS

CROSS-REFERENCE TO RELATED APPLICATIONS

This patent application claims benefit of U.S. Provisional Patent Application No. 60/850,239 filed on Oct. 6, 2006 the entire contents of which is incorporated herein by reference.

STATEMENT REGARDING FEDERALLY SPONSORED RESEARCH OR DEVELOPMENT:

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention relates to an implantable composite prosthesis and method for limiting the incidence of acute postoperative adhesions and calcified scar formation embedded in the prosthesis that can result in a lifetime of post surgical complications and in particular post-operative complications in the field of visceral or parietal soft tissue repair surgery.

2. Background of the Invention

Post surgical adhesions include all non-anatomical fibrous connections accidentally induced by a surgical act during the normal process of cicatrization and may occur in all surgical disciplines regardless of the operation in question. Adhesions can provoke syndromes which can be classed principally as but not necessarily limited to chronic pain, occlusive syndromes, intestinal obstructions and female infertility. Therefore, it is evident that there is a need for a suitable method for preventing the adhesions, and the complications and patient discomfort associated with them.

One solution to reduce acute adhesion consists of separating adjacent internal bodily tissues by interposing a barrier or surgical mesh and barrier layer prosthesis so that during tissue regeneration following surgery no contact exists between the repaired tissue and surrounding organs or other tissue. However, the desired barrier effect of a non-absorbable barrier material can itself be the source of adhesions over the course of time as experienced with current composite prosthesis comprising a barrier made of expanded PTFE (Composix® EX Mesh, Davol/BARD®, Cranston, R.I.); and if it is an absorbable barrier, its absorption must be sufficiently non-inflammatory so as not to be a cicatrizant and cause adhesions itself. In the field of internal medical care, such as internal surgery, there is a need for tissue regeneration devices which may prevent complications such as adhesions in the post-operative healing period.

The approach of utilizing a barrier material is used in U.S. Pat. No. 5,002,551 which discloses a physical barrier formed of a knitted oxidized regenerated cellulose. The patent indicates that other physical barriers include silicone elastomers and absorbable gelatin films. Such physical barriers alone are not sufficient to reinforce the abdominal wall or to repair abdominal wall defects.

As recognized in the art, particularly for visceral and parietal surgery, but also in orthopedic or neurological surgery, the composite prosthesis must also have a certain mechanical strength and permanence allowing it to fulfill a lifetime function as an element of surgical reconstruction. Generally, the known prosthetic fabrics or meshes, particularly in the treatment of parietal insufficiencies, for example hernias, other eventrations and organ suspensions, afford additional mechanical strength to the surgical reconstruction. Most surgical mesh used in the art have the characteristic of being densely knitted and constructed of a monofilament fiber or multifilament yarn so as to present a significant number of very small interstices caused by the knots or loops of the mesh that increase surface area and promote tissue in-growth of scar tissue inside these interstices. Even though scar formation has a purpose in tissue healing, clinically calcified scar tissue is considered pathological and suboptimal to connective tissue that can support blood vessels and act like normal native tissue. Unfortunately, current surgical mesh is constructed of synthetic materials that react with normal tissue invoking a chronic inflammation response and calcified scar encapsulating the mesh prosthesis. It is for this reason that upon contact with the viscera for example, these fabrics promote adhesion which is a feature that limits their use at the so-called preperitoneal or retroperitoneal sites. With some patients the mesh has to be removed due to the complications of scar pathology. In certain procedures, including incisional and umbilical hernia repair and chest reconstruction, the prosthetic mesh may come into direct contact with the sensitive abdominal viscera, creating postoperative adhesions between the mesh and the intestine, potentially leading to intestinal fistulization.

Because of the shortcomings of a non-absorbable barrier or mesh only approach, various approaches to reducing the incidence of postoperative adhesions during healing or chronic scaring arising from the use of prosthetic mesh materials have been used. One traditional solution is to cover the prosthesis with peritoneum or other tissue, where available or adequate to close the defect, to form a biological barrier between the implant and the bowel. Another solution includes the placement of a physical barrier between the surgical site and the surrounding tissue where adhesions are most commonly encountered.

Absorbable combinations of a mesh and other materials or barriers, such as those disclosed in U.S. Pat. No. 4,840,626 and U.S. Pat. Pub. No. 2005/0283256, have been disclosed for use, however there are surgical situations that benefit from having a mesh prosthesis that is not totally absorbed and therefore adds strength to a wound area after it heals.

Barriers having multiple layers, one of which is porous, are disclosed in U.S. Pat. Nos. 5,508,036 and 5,480,436. These barriers are helpful, however there are additional benefits provided by the strength provided by a mesh fabric.

One approach to address the above problems is to combine the features of a non-absorbable mesh with an absorbable barrier sheet. Jenkins et al., "A Comparison of Prosthetic Materials Used to Repair Abdominal Wall Defects", Surgery, Vol. 94, No. 2, August 1983, pg. 392-398, describes a technique of placing an absorbable gelatin film (Gelfilm®) between a piece of Marlex knitted polypropylene monofilament mesh and the abdominal viscera. U.S. Pat. No. 6,451,032 describes a multi-layer prosthesis with one embodiment comprising a mesh and a collagenous material. U.S. Pat. No. 5,593,441 discloses a prosthesis comprising a mesh and an absorbable barrier. However, with these solutions, either through initial contact with the wound, or contact once the barrier is absorbed into the body, the uncoated mesh material stimulates in-growth of scar tissue into and around the mesh. In this case, in-growth is defined as a growth of tissue to or into a fabric, mesh or similar device, connecting an artificial surface to living tissue, but not necessarily extending through it. This in-growth results in fibrotic tissue that, through the fibrotic healing process, is eventually reabsorbed by the body. As a result of this reabsorption, the fibrotic layer formed on the mesh contracts in the direction normal to the mesh and in the plane of the mesh. As the layers contract they pull the mesh with it, causing it to fold and buckle. The result is usually a hard and painful locus of tissue and implant which also increases the instance of adhesion with surrounding tissues.

Microscopic examination of tissue in-growth in both polyester and polypropylene mesh suggests it is the inflammatory potential of the mesh that promotes fibrosis along the plane of the mesh. Therefore, to reduce fibrosis, it is beneficial to reduce the in-growth and inflammatory potential of the mesh.

As opposed to in-growth in the knots or loops of the mesh, tissue through-growth is a healing method that can only be promoted by preventing scar tissue forming in the interstices and promoting connective tissue growth through much larger windows or openings in the mesh fabric. This continuous tissue connection extends through the fabric or mesh or other artificial surface from one living tissue to another. In the case of a mesh and barrier combination, through-growth is confined to tissue connections between adjacent points on the layer of tissue surgically attached to the mesh. Connective tissue through-growth, promoted by the plurality of the larger window pane design, or openings of the mesh, helps decrease the likelihood of infections by preventing microbe proliferation along the surface of densely woven or knitted mesh. Through-growth also does not have the detrimental effects of fibrotic healing related to in-growth. Through-growth supports angiogenesis and further fights infections.

Hydrogels are a material that has a reduced potential for inflammation, and therefore fibrosis, in a tissue. Hydrogels are uniquely biocompatible and contain large amounts of loosely bound water that is free to equilibrate in osmolarity and chemical composition with the surrounding tissue. This exchange of the hydrogel water with the surrounding tissue water makes prosthetics made from hydrogel more tissue-like and hydrophilic, and discourages the attachment of protein markers on the surface of the prosthetic. These features dramatically reduce the inflammatory potential of the prosthetic and reduce the promotion of fibrosis. However, hydrogel-based prosthetics are not currently used in surgical soft tissue repair, primarily because such prosthetics are expected to provide permanent tissue support and most hydrogels are either absorbable or possess little tensile strength.

U.S. Pat. No. 5,593,441 discloses a method for limiting the incidence of postoperative adhesions. A composite of a mesh and a barrier is positioned with the barrier facing away from the defect wall opening. The mesh has a plurality of interstices constructed and arranged to allow tissue in-growth.

U.S. Pat. Pub. No. 2006/0233852 discloses hydrogels reinforced with mesh for use in the repair of tissue defects such as a hernia in order to reduce the incidence of adhesions. The entire contents of U.S. Pat. Pub. No. 2006/0233852 is incorporated herein by reference as if repeated in full herein.

BRIEF SUMMARY OF THE INVENTION

The present invention is a composite prosthesis and method for reinforcing and repairing a weakened tissue defect while limiting the incidence of postoperative adhesions and calcified scar formation. The composite prosthesis is formed of a biologically compatible or biocompatible, flexible and porous implantable mesh suitable for reinforcing tissue and closing tissue defects, particularly in the abdominal cavity, a biologically compatible coating to cover the mesh and a barrier material for physically isolating the tissue defect site from the implantable mesh and areas likely to form adhesions, such as the abdominal viscera. The coated mesh and barrier material are combined by means of incorporating both elements into a single layer fabric or by attaching both materials through means of an adhesive, coating, stitching or insert molding. The barrier material is absorbable or otherwise degradable in a manner which allows tissue through-growth to anchor the implantable mesh material through openings in the implantable mesh.

In one embodiment of the invention, the implantable material comprises at least one sheet of knitted polypropylene monofilament mesh fabric, or similar materials, coated with a hydrogel.

In another embodiment of the invention, the coating closes the knotted or looped interstices and completely surrounds the multifilament structures of the mesh to ensure that scar tissue does not form in the small interstices and the coating also reduces the total mesh surface area exposed to tissue compared to an uncoated surface. In one embodiment, the biocompatible character of the hydrogel coating reduces the negative tissue reactions to polypropylene, polyester or other synthetic materials of uncoated meshes.

It is an object of this invention to provide a composite prosthesis comprising a coated mesh having at least one opening through a first surface and a second surface of the coated mesh, the coated mesh comprising a mesh and a biocompatible coating substantially covering the mesh. In one embodiment, the barrier material is comprised of a bioabsorbable segmented copolymer comprising a first component which is a polyalkylene glycol and a second component which is a polyester formed from an alkylene glycol having from 2 to 8 carbon atoms and a dicarboxylic acid and the barrier material is selected from the group consisting of a non-porous layer and a porous layer in which essentially all of the pores have a pore size no greater than 3 microns. In one embodiment, the mesh comprises a knitted mesh and the barrier material is attached to at least one surface of the coated mesh and the barrier material biocompatible coating is formed by curing a polyalkylene oxide polyol end capped with isocyanate, the polyalkylene oxide polyol having from about 70% to about 95% ethylene oxide groups and the remainder propylene oxide.

It is an object of this invention to provide a composite prosthesis comprising a coated mesh having at least one opening through a first surface and a second surface of the coated mesh, the coated mesh comprising a mesh and a biocompatible coating substantially covering the mesh and a barrier material comprising a biocompatible membrane constructed and arranged to cover at least one surface of the coated mesh. In one embodiment, the barrier material comprises a poly lactide polymer or co-polymer. In one embodiment, the mesh coated mesh comprises a knitted mesh and the barrier material is attached to at least one surface of the coated mesh and the barrier material biocompatible coating is formed by curing a polyalkylene oxide polyol end capped with isocyanate, the polyalkylene oxide polyol having from about 70% to about 95% ethylene oxide groups and the remainder propylene oxide.

It is among the general objects of the invention to provide a composite prosthesis which combines the attributes of a surgical mesh fabric and of a physical barrier.

It is a further object of the invention to provide a composite prosthesis for repairing ventral hernias and for reconstructing the chest wall which limits the incidence of postoperative adhesions and intestinal fistulization.

It is a further object of the invention to provide a composite prosthesis which minimizes inflammatory stimuli to the tissue surrounding the surgical opening and minimized the inflammatory response of other areas of potential adhesions such as the abdominal viscera.

It is another object of the invention to provide a composite prosthesis which provides an implantable material that is retained near the surface of the tissue opening to continue to reinforce the tissue wall.

It is a further object of the invention to provide a composite prosthesis which may be custom shaped, sized and affixed during surgery without destroying the integrity of the device.

An additional object of the invention is to provide a prosthesis which is sufficiently flexible to conform to the surgical site.

It is a further object of the invention to provide methods of utilizing embodiments of a composite prosthesis that limits the incidence of postoperative adhesions.

It is another object of the invention to provide a method for limiting the incidence of postoperative adhesions arising from a repair of a defect in a tissue comprising the steps of providing a composite prosthesis comprising a coated mesh and a barrier and positioning the composite prosthesis to cover the defect whereby the formation of postoperative adhesions is limited.

An additional object of the invention is to provide a method of limiting the incidence of postoperative adhesions arising from a repair of a defect in a tissue comprising the steps of providing a composite prosthesis comprising a coated mesh and a barrier and positioning the composite prosthesis with the coated mesh away from the defect and the barrier material positioned between defect and the coated mesh whereby the formation of postoperative adhesions is limited.

It is a further object of the invention to provide a method of making a composite prosthesis comprising the steps of coating at least one fiber with a biocompatible coating to form a coated mesh and attaching an adhesion-resistant barrier material to the coated mesh.

Other objects and features of the present invention will become apparent from the following detailed description.

DETAILED DESCRIPTION OF THE INVENTION

While this invention is capable of being implemented in many different embodiments, there is shown in the drawings, and will herein be described in detail, several specific embodiments, with the understanding that the present disclosure can be considered as an exemplification of the principles of the invention and is not intended to limit the invention to the embodiments illustrated.

The invention will be described by way of example in relation to a composite prosthesis intended for use in parietal surgery, in the repair of eventrations or hernias. These descriptions are used as examples of embodiments and use of these embodiments of the invention and are not intended to limit embodiments or uses.

Figure 1A:
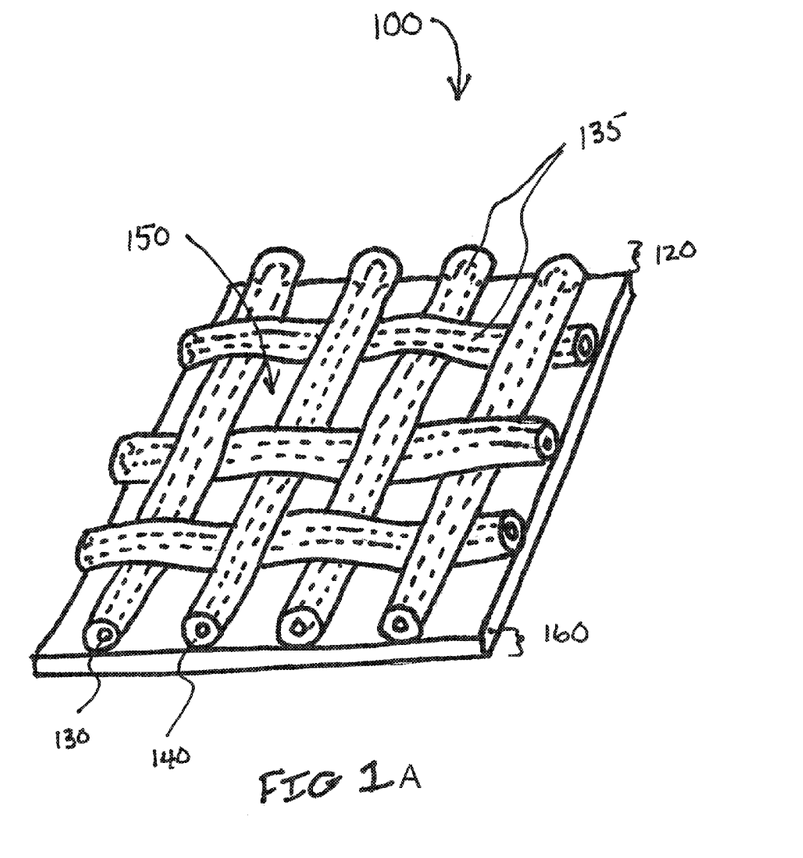
FIG. 1A is a top perspective view of one embodiment of the composite prosthesis.

The Apparatus:

Referring to FIG. 1A, the composite prosthesis 100 for limiting the incidence of postoperative adhesions includes a tissue infiltratable mesh 135 comprising one or more fibers 130 coated with a biocompatible coating 140 creating a coated mesh 120. The coated mesh 120 is covered by an adhesion resistant bioabsorbable barrier material 160. The coated mesh 120 construction creates a plurality of pores, windows or openings 150 which are of sufficient size and orientation to allow sufficient tissue through-growth to secure the composite prosthesis 100 to a defect site once the stimulus for tissue adhesion formation has subsided and the barrier material 160 has been absorbed. The integration of the barrier material 160 and the coated mesh 120 separates the tissue defect from the area of potential tissue adhesion. The composite combines the strength, handling and adhesive properties of a prosthetic mesh with the low adhesion incidence of a physical barrier.

The term "biocompatible" as used herein refers to biologically compatible materials that do not elicit a toxic or severe immunological response following implantation or ingestion in a body or other organism.

The term "bioabsorbable" as used herein encompasses the complete resorption of the materials of the apparatus by the body as well as a breakdown of the structure of the apparatus without complete resorption of the apparatus; i.e., the structure of the apparatus is broken down into a plurality of pieces which are not completely resorbed.

The relatively flat composite prosthesis 100 is sufficiently pliable to allow a surgeon to manipulate the shape of the prosthesis to conform to the anatomical site of interest and to be sutured, glued, tacked or stapled there. Alternatively, the composite prosthesis 100 may be pre-formed into a more complex shape, such as a tapered plug for filling and occluding a ruptured wall. The shape and size of the composite prosthesis 100, and of the respective coated mesh 120 and barrier material 160, may vary according to the surgical application as would be apparent to those of skill in the art.

The Apparatus Mesh and Mesh Coating:

Referring to FIG. 1A, in one embodiment, the mesh 135 is formed from a knitted fabric that contains openings 150. A suitable fabric for the mesh 135 includes a sheet of knitted polypropylene monofilament mesh fabric such as Marlex® mesh available from C. R. Bard, Inc. Other surgical materials suitable for the mesh 135 include, but are not limited to Prolene®, Dacron®, Teflon®, Merselene® and Parietex™ by Covidien. It also is contemplated that the mesh 135 may be formed from porous membranes, multifilament yarns and that woven, molded and other recognized methods of forming a prosthetic mesh with openings, windows or pores are suitable. It is also contemplated that the mesh 135 may be formed from materials such as fibers and non-porous membranes that when coated with a biocompatible coating, as described below, are capable of possessing the features of porous membranes or prosthetic meshes. Examples of suitable materials for the mesh 135 include, but are not limited to those described in at least U.S. Pat. Nos. 3,054,406; 3,124,136; 4,193,137; 4,347,847; 4,452,245; 4,520,821; 4,633,873; 4,652,264; 4,655,221; 4,838,884; 5,002,551; and European Patent Application No. 334,046 all of which are incorporated by reference. Monofilament and multifilament polyester mesh materials are also contemplated.

Figure 1B:
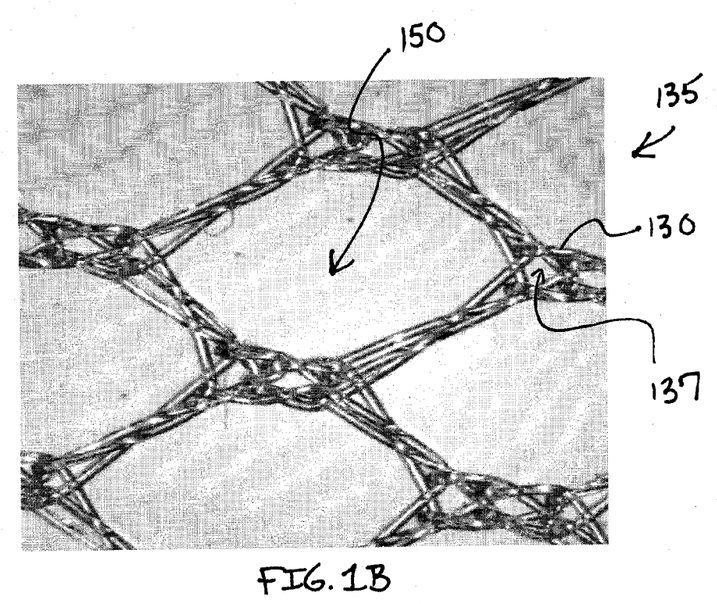
FIG. 1B is a top view of one embodiment of a mesh.

FIG. 1B illustrates one embodiment of a mesh 135 showing the openings 150 of the mesh, the mesh fibers 130 and interstices 137 formed in the mesh 135.

Referring to FIG. 1A, the fibers 130 of the mesh 135 preferably are coated with a non-absorbable, biocompatible coating 140 such as a hydrogel creating a coated mesh 120. This coating 140 reduces the inflammatory reaction caused by the coated mesh 120 against tissue. When mixed with an aqueous solution, the hydrogel encapsulates the fibers 130 of the mesh 135. The mesh 120 with a coating 140 can be made such that no portion of the fibers 130 are exposed beyond the coating 140. Thus the chemical and physical composition of the fiber 130 does not necessarily contribute to a tissue response when placed in a mammalian body.

Figure 1C:
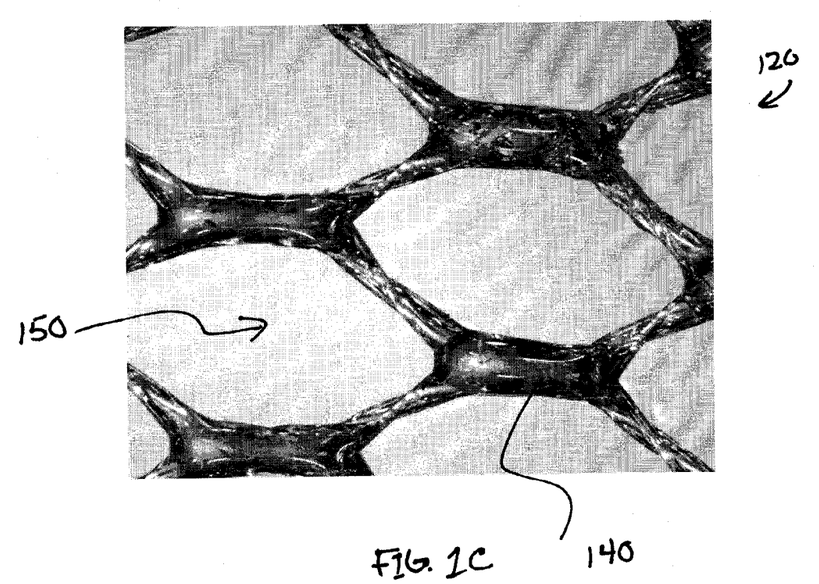
FIG. 1C is a top view of one embodiment of a coated mesh.

FIG. 1C illustrates one embodiment of a coated mesh 120 showing the openings 150 of the coated mesh 120 and the biocompatible coating 140 covering the mesh fibers and the interstices of the mesh.

In one embodiment, the coating 140 is a hydrogel. A preferred hydrogel for coating the mesh 135 is the surgical adhesive described in U.S. Pat. Pub. No. 2005/0129733, which is herein incorporated by reference in its entirety.

Examples of other suitable coatings 140 include, but are not limited to those non-absorbable prepolymers described in at least U.S. Pat. No. 4,990,357, U.S. Pat. Pub. No. 2002/0049503 and U.S. Pat. application Ser. No. 11/010,629, published as U.S. Pub. No. 2005/0129733 all of which are incorporated by reference in their entirety. A hydrogel invites little fibrosis, because there is little protein absorption which is involved in cell attachment and, hence, little fibrosis. The hydrophilicity of the coating prevents fibrous tissue adhesion directly to the surface of the coating and promotes un-stimulated tissue growth around this coating. Un-stimulated tissue growth allows the through-growth of tissue into the openings of the coated mesh 120 which is different than normal in-growth into the interstices of the mesh. Through-growth does not adhere or scar the tissue to a foreign surface such as the mesh and therefore does not promote fibrosis along the plane of the mesh. Through-growth is a continuous tissue to tissue connection extending through or around a foreign surface without attaching to the foreign surface.

In one embodiment of the composite prosthesis 100, the coating 140 comprises a non-absorbable hydrogel. Suitable non-absorbable hydrogel compositions suitable for the mesh 135 coating are described in U.S. Pat. No. 6,296,607, in U.S. Pat. application Ser. No. 10/020,331, published as Pub. No. 2003/0135238 and in U.S. Pat. application Ser. No. 11/092,396, published as Pub. No. 2005/0215748 each of which is incorporated by reference in their entirety. While these compositions are preferred, there are other types of hydrogels that may be used in embodiments of the invention. Some of these other types are described in U.S. Pat. No. 5,410,016 which is herein incorporated by reference.

Prepolymers of polyurethanes form one embodiment of hydrogels used as coating 140 in one embodiment of this invention. These prepolymers are formed by endcapping triols, or triolized diols, with low molecular weight diisocyanate, and then reacting the product of these steps with an excess of water. When the polyol component is a polyalkylene oxide (PAO) constructed from approximately 75% (70%-95%) ethylene oxide monomers and about 25% (5%-30%) propylene oxide monomers, the resulting hydrogel can contain up to 90% water and achieve desirable stability and strength characteristics. The PAO can be made as a diol (two armed) and later made capable of crosslinking by trimerization with a low molecular weight triol (such as trimethylol propane, TMP) or a higher-functionality material. The PAO can also be made as a tri-armed structure by starting with a trifunctional starter, such as TMP.

One embodiment of prepolymers are the product of reacting about 20% by weight to about 40% by weight TDI (toluene diisocyanate), 65% by weight to about 85% by weight polyalkylene oxide (PAO) diol and about 0.5% by weight to about 2% by weight TMP (trimethylol propane). Preferably, but not limiting embodiments, the composition is the product of reacting in weight ratios about 20% to about 25% TDI, 70% to about 80% PAO diol and about 0.7% to about 1.2% TMP. Most preferably, but not limiting embodiments, the composition is the result of reacting about 23% to about 25% TDI, about 73% to about 77% diol and about 0.7% to about 1.0% TMP. Most preferably, the composition is the result of reacting about 24% TDI, 75% diol and about 0.7% to 1.0% TMP. In the above reaction products, a preferred diol is 75% polyethylene glycol and 25% polypropylene glycol, but can have values in the range of about 70%-95% ethylene oxide monomers and 5%-30% propylene oxide monomers.

Other embodiments are the product of reacting about 20% by weight to about 40% by weight IPDI (isophorone diisocyanate; an aliphatic diisocyanate with a slower reaction rate than TDI), 65% by weight to about 85% by weight diol and about 1% by weight to about 10% by weight TMP. Preferably, but not limiting embodiments, the composition is the product of reacting in weight ratios about 25% to about 35% IPDI, 70% to about 80% diol and about 2% to about 8% TMP. Most preferably, but not limiting embodiments, the composition is the result of reacting about 25% to about 30% IPDI, about 70% to about 75% diol and about 1% to about 8% TMP. Most preferably, but not limiting embodiments, the composition is the result of reacting about 25% IPDI, 70% diol and about 1% to 2% TMP. In the above reaction products, a preferred diol is 75% polyethylene glycol and 25% polypropylene glycol.

Thus, in the preferred hydrogel-forming compositions described above, the coating material is a polyol prepolymer containing a polyalkylene oxide polyol end capped with isocyanate. Preferably, the polyol is tri-functional as described, and polyalkyene oxide monomers in the composition consist of from about 70% to about 95% ethylene oxide monomer with the rest of the monomers being propylene oxide.

Other non-absorbable, biocompatible materials may be utilized as the coating 140 as would be apparent to those of skill in the art, the ultimate selection depending upon the composition of the mesh 135 and the barrier material 160.

It is contemplated that the embodiments of the coated mesh include coating the fibers or other material of the mesh prior to creating the mesh as well as coating the fibers or other materials of the mesh after they are formed as the mesh. For example, single fibers can be coated with the biocompatible coating to form a coated mesh as well as using single fibers to create a mesh that can then be coated with a biocompatible coating to form a mesh.

The Apparatus Barrier Material:

Referring to FIG. 1A, the barrier material 160 comprises an anti-adhesive bioabsorbable segmented copolymer comprised of a bioabsorbable, biodegradable or bioerodable polymer. In one embodiment, the barrier material 160 is formed as a generally planar, non-porous (i.e., essentially having no pores) membrane which acts as a barrier layer. Preferably, the barrier material 160 is non-porous however it is also contemplated that pores can be present in the barrier material 160 provided that the pores do not interfere with the barrier material's ability to reduce the incidence of adhesion. When pores are present, it is preferable that the pores of the barrier material 160 are less than 3 microns. The barrier material 160, in general, also prevents the in-growth of tissue and has a thickness of from about 5 microns to about 300 microns, preferably from about 10 microns to about 300 microns.

The polymer of the barrier material 160 is one which is bioabsorbable, biodegradable, or bioerodable, i.e., the polymer is broken down gradually by the body after implantation. After a period of time, which may vary depending upon various factors such as the thickness of the barrier material 160 layer, the proportion of the components of the polymer, and the specific use of the polymer, the polymer loses its unitary structure. For example, the polymeric device breaks into pieces, and may eventually be completely resorbed. Preferably, the polymer is bioabsorbable in addition to being biodegradable; i.e., the polymer is resorbed by the body such that the polymeric device becomes essentially non-detectable at the site of implantation.

Polymers which may be employed to form the barrier material 160 include, but are not limited to, polyethers (both substituted and unsubstituted); poly (hydroxyethyl methacrylate); polyurethanes; polyamides; polyanhydrides; polysulfones; polycaprolactones; polyglycolides; polylactides, such as, for example, polylactic acid; polyphosphazenes; poly amino acids; poly-orthoesters; polyiminocarbonates; polytrimethylene carbonates; polyhydroxymethacrylates; polyhydroxybutyrate; polyglyconate; polydioxanone; polyhydroxyvalerate; polyhydroxybutyrate/polyhydroxyvalerate copolymers; polyester urethanes; polyether urethanes, and polyurethane urea. In one embodiment, the polymer may be a copolymer formed from any combination of the above components. The polymer may also be a polymer of a "soft" component selected from the group consisting of polyethers (both substituted and unsubstituted) and poly (hydroxyethyl methacrylate) or a "hard" component selected from the group consisting of urethanes, amides, and esters. It is also contemplated that the polymer can be in the form of a hydrogel. A hydrogel, because of its hydrophilicity, invites little fibrosis, because there is little protein absorption which is involved in cell attachment and, hence, little fibrosis. Suitable materials for the barrier material 160 include but are not limited to the polymers described in U.S. Pat. No. 5,508,036 and U.S. Pat. No. 5,480,436 both of which are herein incorporated by reference in their entirety.

In one embodiment, the barrier material 160 comprises a poly lactide polymer or co-polymer and, more preferably, comprises poly (L-lactide-co-D,L-lactide) 70:30 Resomer LR708 manufactured and supplied from Boehringer Ingelheim KG of Germany. Suitable materials for the barrier material include but are not limited to the materials described in U.S. Pat. No. 6,673,362 and U.S. Pat. No. 6,531,146 both of which are herein incorporated by reference in their entirety.

It is contemplated that the barrier material 160 can comprise materials such as, but not limited to Seprafilm® sold by Genzyme, Edicol™ made by Devro, Pelvicol® as made by BARD and Oxiplex® Barrier or Medishield™ made by Fziomed or similar materials.

In one alternative, the barrier material 160 may be coated with an adhesive such as, but not limited to, cellulose (such as carboxymethyl cellulose, or CMC, and hydroxypropyl methyl cellulose, or HPMC); mucoadhesives, such as, but not limited to, mucin, mucopolysaccharides, polycarbophil, tragacanth, sodium alginate, gelatin, pectin, acacia, and providone; acrylates (such as polyacrylic acid and methyl methacrylate); polyoxyethylene glycol having a molecular weight of from about 100,000 to about 4,000,000; mixtures of zinc oxide and eugenol; a fibrin-glue layer; a chitosan layer; and glucosamine. Such a coating improves initial adhesion of the barrier material 160 of the composite prosthesis 100 to tissue, such as the peritoneum.

In another embodiment, the adhesive may be admixed with the polymer in the barrier material 160 of the device, as the barrier material 160 is being formed. In such a manner, a portion of the adhesive will be exposed on the desired surface of the barrier material 160 upon formation of the barrier material.

The barrier material 160 is preferably, but not limited to being formed of a translucent material which allows the physician to observe the location and integrity of the composite prosthesis during implantation. Holes may be formed through the barrier to facilitate passage of neutrophiclic granulocytes, reducing the incidence of infection. The holes should have dimensions sufficient to permit neutrophilic granulocytic transport without detrimentally affecting the adhesion resistance of the composite.

Other surgical adhesion resistant materials also may be used as would be apparent to those of skill in the art.

Figure 2A:
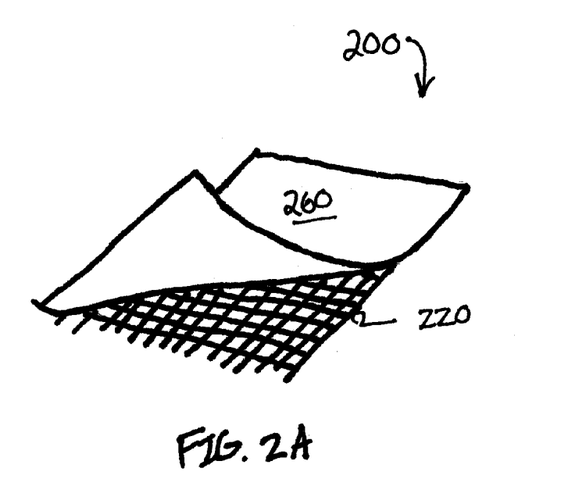
FIG. 2A is an isometric view of one embodiment of the composite prosthesis with the mesh and barrier material attached with a portion of the barrier meterial held away from the mesh.
Figure 2B:
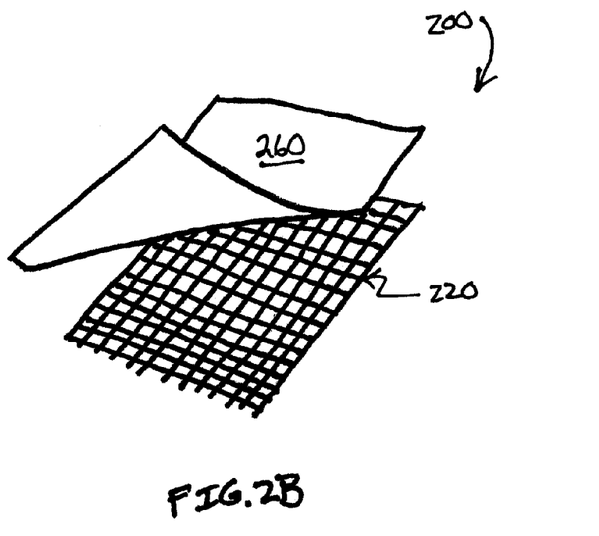
FIG. 2B is an isometric view of one embodiment of the composite prosthesis with the mesh and the barrier material not attached.

Integration:

Referring to FIG. 2A, the coated mesh 220 and the barrier material 260 of the composite prosthesis 200 can be integrally attached or, as shown in FIG. 2B, the two layers can be separate.

Figure 3A:
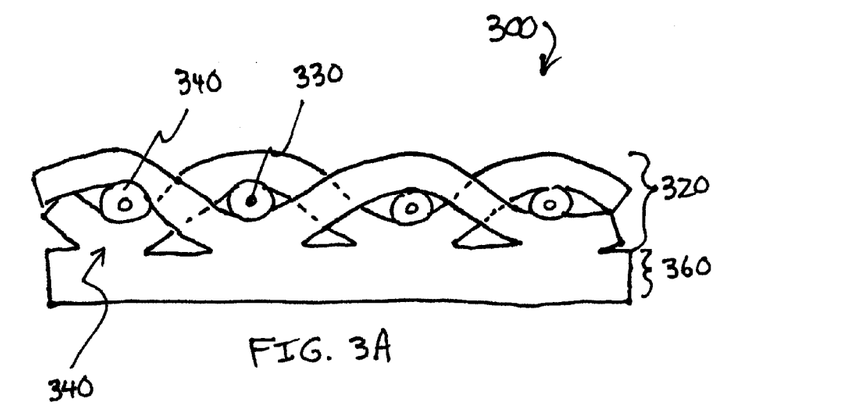
FIG. 3A is a cross-section view of one embodiment of the composite prosthesis showing the mesh and barrier material attached by a biocompatible coating.
Figure 3B:
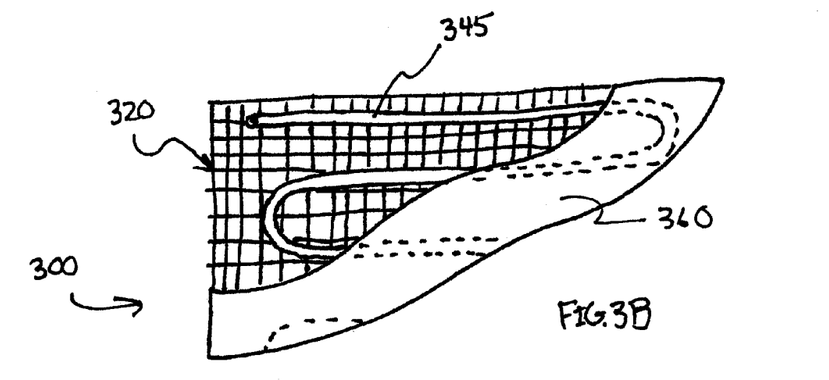
FIG. 3B is a top view, in partial section view, of one embodiment of the composite prosthesis with a portion of the barrier material removed showing the mesh and barrier material attached by an adhesive.
Figure 3C:
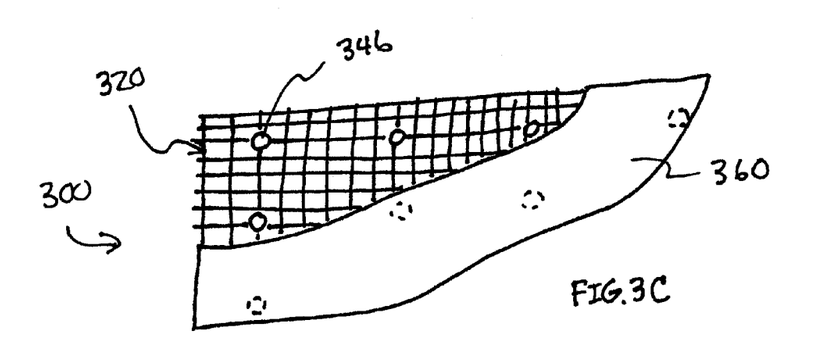
FIG. 3C is a top view, in partial section view, of one embodiment of the composite prosthesis with a portion of the barrier material removed showing the mesh and barrier material attached by an adhesive.

FIGS. 3A-3C show embodiments of the composite prosthesis 300 where the coated mesh 320 and the barrier material 360 are integrally attached or otherwise connected. In one embodiment shown in FIG. 3A, this connection is provided by attaching the barrier material 360 to the coated mesh 320 by using the coating 340 on the mesh fibers 330 as an adhesive. This can be accomplished by polymerizing the coating 340 on the fibers 330 or the coated mesh 320 and the barrier material 360 at the same time. A preferred hydrogel for joining the barrier material 360 to the coated mesh 320 is the surgical adhesive described in U.S. Pat. Pub. No. 2005/0129733. These prepolymers form a hydrogel matrix when mixed with an aqueous solution which bonds to the sheet of barrier material. Other adhesives may be utilized as would be apparent to those of skill in the art, the ultimate selection depending upon the composition of the mesh and the barrier material.

By way of further example, a mesh may be coated as described in the example of U.S. Pat. Pub. No. 2006/0233852 by applying the preferred non-absorbable hydrogel-forming polyol compositions in solution to a mesh (with or without openings pre-formed in the mesh as contemplated in U.S. Pat. Pub. No. 2006/0233852) and, prior to curing of the coating, applying the barrier material to the coated uncured mesh. As the coating cures, it will also adhere the barrier material to the coated mesh.

Alternatively as shown in FIGS. 3B and 3C, additional adhesive may be applied in a grid-like pattern of dots or beads. In a representative arrangement shown in FIG. 3C, spaced dots 346 form an effective joint between the coated mesh 320 and the barrier material 360. A serpentine pattern 345 as shown in FIG. 3B or staggered configurations are also possible. Various other shapes, sizes and patterns of adhesives or other attachment means such as, but not limited to sewing, may be used as would be apparent to those of skill in the art.

Embodiments of the present invention therefore provide a composite prosthetic, amongst which are certain of the following advantages. The composite prosthesis combines the strength of a mesh material and the low adhesion incidence of a physical barrier. If a coated mesh with openings as contemplated in U.S. Pat. Pub. No. 2006/0233852 is used, after a bioabsorbable barrier has been absorbed or resorbed, the composite may be anchored in place by tissue through-growth through the coated mesh openings after the barrier layer is absorbed by the body. The specific pattern of attachment (adhesive, molding, stitching, etc.) of the mesh and barrier material can provide a dimensional strength to the prosthesis.

The composite of the present invention is particularly indicated for repair of ventral hernias (incisional and umbilical) and chest wall defects where it is more common for the prosthetic mesh to be exposed to the abdominal viscera due to insufficient or unavailable autogenous tissue. The non-inflammatory coating prevents the mesh fabric from causing inflammation of the abdominal viscera, reducing the incidence of intestinal adhesion and fistulization. It also is contemplated that the composite prosthesis would be indicated for use in laparoscopic procedures, particularly intraperitoneal applications where the peritoneum would not be available to provide a natural barrier between the implant and the intestine.

It is contemplated that embodiments of the prosthesis can be sized and shaped to be used with specific surgical procedures that require uniquely sized and shaped embodiments of the present invention.

Other embodiments of the composite prosthesis comprise the herein described embodiments of a coated mesh and absorbable barrier material having an additional non-absorbable layer of barrier material. This non-absorbable layer of barrier material is placed on the surface of the coated mesh opposite of the surface against which the barrier material is placed. Examples of suitable materials to create the non-absorbable barrier material include, but are not limited to those non-absorbable prepolymers described in U.S. Pat. Pub. No. 2006/0233852.

The device may also contain pharmaceutical agents (e.g., proteins, nucleic acids, antibiotics, etc.) which are placed in the device with an acceptable pharmaceutical carrier. Such agents may diffuse out of the device and into the body after implantation, and/or may be released internally upon degradation of the device, thereby providing a desired therapeutic effect.

Figure 6:
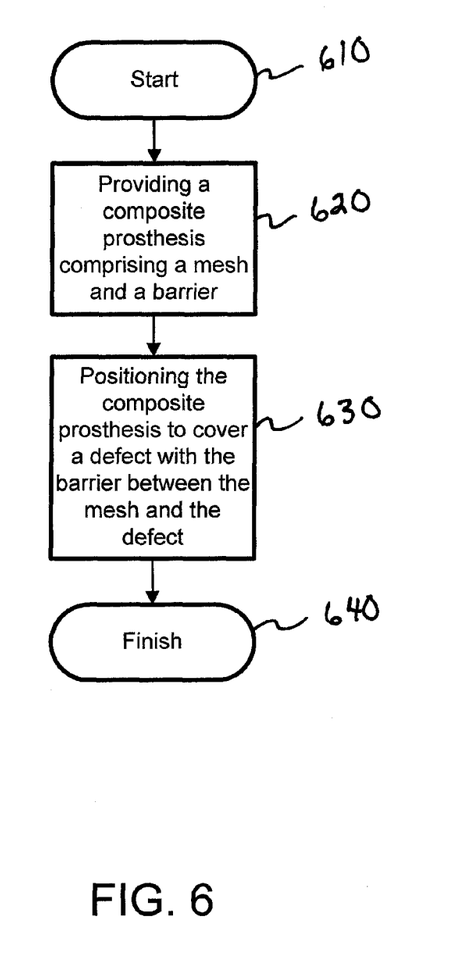
FIG. 6 is a process diagram illustrating one embodiment of a method of using the composite prosthesis.

Method of Operation:

FIG. 6 is a process diagram illustrating one embodiment of a method of using the composite prosthesis. The method starts with step 610 and is followed by step 620 of providing a composite prosthesis comprising a coated mesh and a barrier material. Step 630 comprises positioning the composite prosthesis to cover the defect. The method is concluded with step 640.

Figure 4:
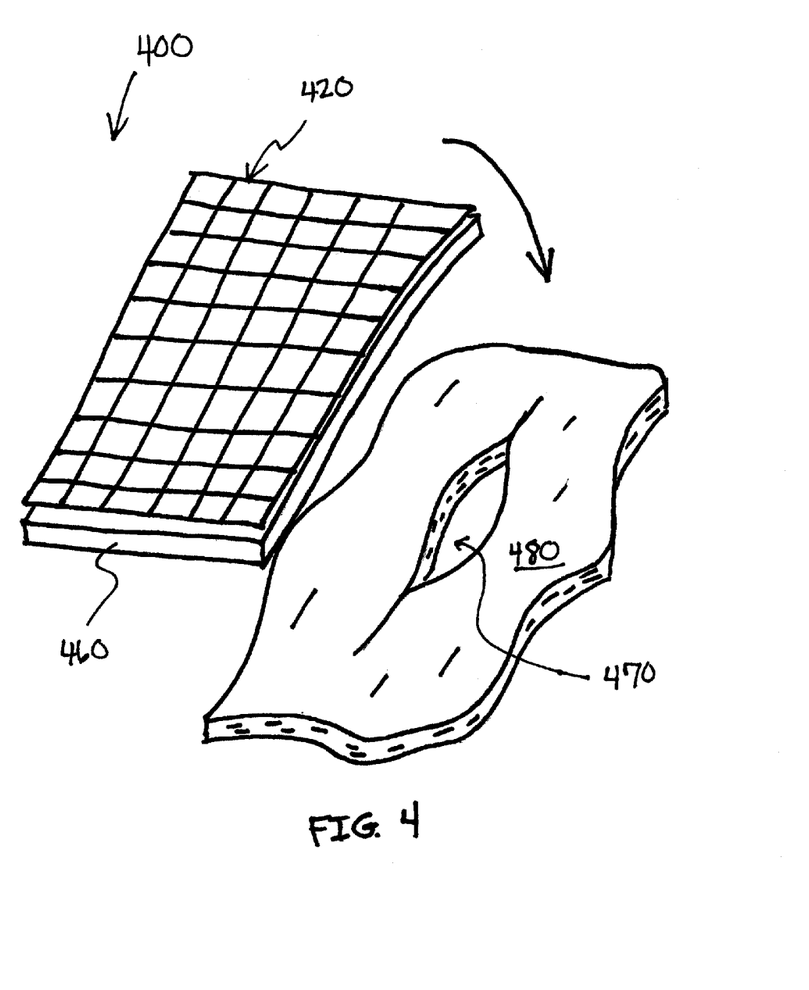
FIG. 4 is a side, perspective view of one embodiment of the composite prosthesis and its positioning relative to a tissue defect.

This embodiment is further illustrated by, but not limited to, the embodiment in FIG. 4. Referring to FIG. 4, the composite prosthesis 400 can be used to repair a defect 470 in a wall 480 of a patient's body cavity that exposes a visceral surface. To repair the defect 470, a medical professional inserts the composite prosthesis 4400 through opening 470 and into the body cavity. The composite prosthesis 400 is positioned such that coated mesh surface 420 faces the visceral surface and the barrier material 460 faces the tissue wall 480 and covers the defect 470. Once the composite prosthesis 400 is positioned, the medical professional attaches the composite prosthesis 400 to the tissue surrounding the defect 470 with sutures, staples, tacks, glue or other attaching means.

Figure 5:
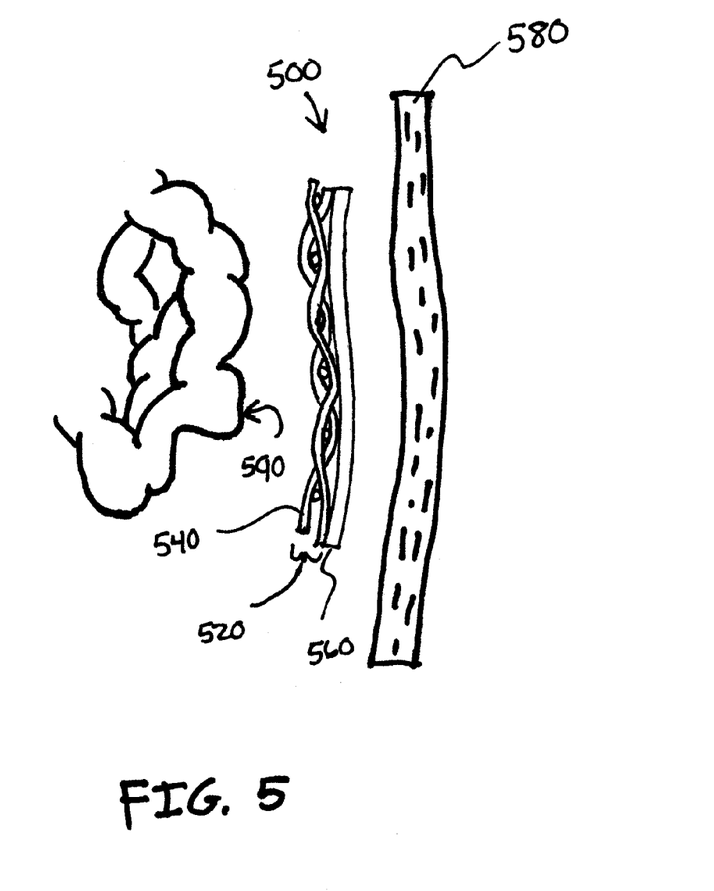
FIG. 5 is a side cut-away view of one embodiment of the composite prosthesis illustrating one proposed position of the composite prosthesis positioning relative to a tissue defect and surrounding organs.

As used in the repair of ventral hernias and in chest wall reconstruction, as illustrated in FIG. 5, the barrier material 560 isolates the abdominal viscera 590 from the healing process of the defect and the coated mesh 520 reduces the inflammatory response characteristic of the mesh fibers. Together, these features prevent intestinal adhesion and fistulization which may result from an inflammatory reaction of the visceral surface 590 and the mesh throughout the healing process.

Referring to FIG. 5, as part of the normal healing process, the barrier material 560 is absorbed by the body, leaving the coated mesh 520 between the tissue 580 and the visceral surface 590. During this healing, the barrier material 560 is placed against the defect, and because it is a hydrogel, it minimizes the stimulation of the defect tissue. By the time the barrier material 560 has been absorbed, the defect in the tissue 580 has healed to an extent (e.g., a new peritoneal surface has formed over the defect) that the likelihood of adhesions forming between viscera 590 and coated mesh 520 is minimal. The barrier material 560 may be absorbed by the body over a period of at least about 14 days from an initial implantation of the prosthesis. In addition to the adhesion resistance provided by the barrier material 560, the coating 540 covering the mesh and mesh fibers provides a second defense against adhesion prevention by further minimizing the stimulation of the defect tissue 580.

After the barrier material 560 is absorbed by a patient's body, the coated mesh 520 of the composite prosthesis 500 becomes incorporated into the tissue wall 580 by in-growth (if the coated mesh is constructed to permit such in-growth) or more preferably by through-growth of tissue 580 through the openings or windows formed in the coated mesh 520 for that purpose as described in U.S. Pat. Pub. No. 2006/0233852, in which tissue grows through the openings and around or over the coated mesh rather than into the interstices of the mesh, the mesh coating or the mesh fibers. While implantation with the barrier material 560 facing the defect to be repaired is preferred and described herein, it is also contemplated that the barrier material 560 could be implemented facing the viscera 590, with the coated mesh 520 facing the defect.

Examples of uses of the devices of the present invention include, but are not limited to, barriers and prostheses between the internal female reproductive organs (e.g., uterus, fallopian tubes, ovaries); barriers and prostheses between the internal female reproductive organs and the peritoneum; barriers and prostheses for used during laparoscopy; barriers and prostheses between periodontal tissue; barriers and prostheses between cartilages or between cartilage and bone; barriers and prostheses between digestive organs; spinal barriers and prostheses; barriers and prostheses between digestive organs and peritoneum; barriers and prostheses between the epicardium and surrounding structures such as the pericardium, mediastinal fat, pleura, and sternum; barriers between tendons and tendon sheaths, such as those in the wrist and ankle; bone fracture wraps; barriers between muscle tissue and bone; barriers and prostheses between the esophagus and mediasternum; barriers and prostheses between the gall bladder or pancreas and the peritoneum; and barriers and prostheses for scrotal surgery.

Figure 7:
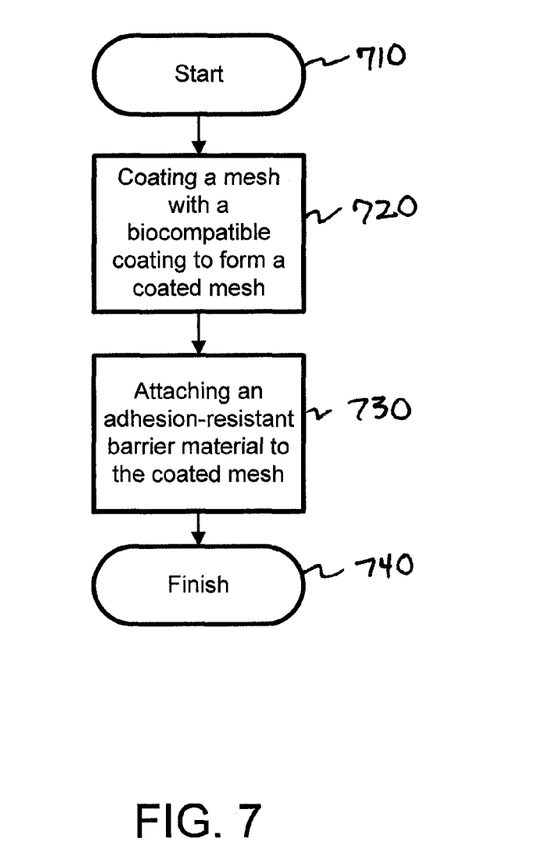
FIG. 7 is a process diagram illustrating one embodiment of a method of making the composite prosthesis.

Making the Composite Apparatus:

FIG. 7 illustrates one embodiment of a method of making the composite prosthesis. This embodiment starts with step 710 and is followed by step 720 comprising a step of coating a mesh with a biocompatible coating to form a coated mesh. Next, step 730 comprises attaching the adhesion-resistant barrier material to the coated mesh. The method is complete with step 740. The composition of the mesh, biocompatible coating and barrier material compositions include, but are not limited to those described and referenced herein.

The method described above illustrates one method of creating several embodiments of the composite prosthesis to include, but not limited to those shown in FIGS. 1, 2A, 3B and 3C.

Other embodiments of the method described are contemplated, including but not limited to methods of making the embodiment illustrated in FIG. 2B, where the coated mesh and the barrier material are made separately.

In other embodiments, including but not limited to the embodiment illustrated in FIG. 3A, the step of coating the mesh and the step of attachment of the coated mesh to the barrier material can occur nearly simultaneously or within a sufficient time period that the barrier material can be applied to the coated mesh before the coating has cured and thereby attaching the barrier to the coated mesh.

With respect to the above description then, it is to be realized that the optimum chemical and mechanical relationships for the elements of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact embodiment and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

Other embodiments of this invention are within the scope of the following claims.

We claim:
1. A composite prosthesis comprising:
a coated mesh having at least one opening through a first surface and a second surface of the coated mesh;
the coated mesh comprising a mesh, and
a cured biocompatible coating substantially surrounding each filament of the mesh,
wherein the biocompatible coating is a non-absorbable cyanate-terminated hydrophilic prepolymer comprising:
a copolymer comprising polyether monomers and from 5% to 30% of propylene oxide monomers;
from 20 to 40 wt. % of at least one polyisocyanate selected from the group consisting of 2,4-toluene diisocyanate, 2,6-toluene diisocyanate, and isophorone diisocyanate; and
from 1.0 to 10 wt. % of trimethylolpropane; and
a barrier material comprising a biocompatible membrane constructed and arranged to cover at least one surface of the coated mesh, wherein the barrier material is a bioabsorbable material adhered to the mesh by the cured prepolymer.

2. The composite prosthesis according to claim 1 wherein the mesh comprises a knitted mesh and the barrier material is attached to at least one surface of the coated mesh.

3. The composite prosthesis according to claim 2 wherein the barrier material is attached to the coated mesh by the biocompatible coating.

4. The composite prosthesis according to claim 1 wherein the barrier material is comprised of a bioabsorbable segmented copolymer comprising a first component which is a polyalkylene glycol and a second component which is a polyester formed from an alkylene glycol having from 2 to 8 carbon atoms and a dicarboxylic acid; and the barrier material is selected from the group consisting of a non-porous layer and a porous layer in which essentially all of the pores have a pore size no greater than 3 microns.

5. The composite prosthesis according to claim 1 wherein the barrier material comprises a poly lactide polymer or copolymer.

6. The composite prosthesis according to claim 1 wherein the biocompatible coating is a hydratable polymer.

7. The composite prosthesis according to claim 1 wherein the prepolymer is tri-functional.

8. The composite prosthesis according to claim 1 wherein the barrier material is glued to the coated mesh.

9. The composite prosthesis according to claim 1 wherein the coated mesh comprising the barrier material is formed by applying the barrier material before the coating applied to the mesh has cured.

10. The composite prosthesis according to claim 1 wherein the prepolymer is a hydrogel.

11. The composite prosthesis according to claim 1 wherein the mesh is a multifilament mesh.

12. The composite prosthesis according to claim 1 wherein the mesh is a monofilament mesh.

13. The composite prosthesis according to claim 1 wherein the mesh is a polypropylene mesh.

14. A composite prosthesis comprising:
a coated mesh having at least one opening through a first surface and a second surface of the coated mesh;
the coated mesh comprising a mesh and a cured biocompatible coating substantially surrounding each filament of the mesh, wherein the biocompatible coating is a non-absorbable cyanate-terminated hydrophilic prepolymer comprising:

a copolymer comprising polyether monomers and from 5% to 30% of propylene oxide monomers;

from 20 to 40 wt. % of at least one polyisocyanate selected from the group consisting of 2,4-toluene diisocyanate, 2,6-toluene diisoscyanate, and isophorone diisocyanate; and from 1.0 to 10 wt. % of trimethylolpropane; and a bioabsorbable barrier material comprising a biocompatible membrane constructed and arranged to cover at least one surface of the coated mesh.

15. The composite prosthesis according to claim 14 wherein the prepolymer is tri-functional.

16. The composite prosthesis according to claim 14 wherein the mesh comprises a knitted mesh and the barrier material is attached to at least one surface of the coated mesh.

17. The composite prosthesis according to claim 14 wherein the barrier material is attached to the coated mesh by the biocompatible coating.

18. The composite prosthesis according to claim 14 wherein the barrier material is comprised of a bioabsorbable segmented copolymer comprising a first component which is a polyalkylene glycol and a second component which is a polyester formed from an alkylene glycol having from 2 to 8 carbon atoms and a dicarboxylic acid; and the barrier material is selected from the group consisting of a non-porous layer and a porous layer in which essentially all of the pores have a pore size no greater than 3 microns.

19. The composite prosthesis according to claim 14 wherein the barrier material comprises a poly lactide polymer or co-polymer.

20. The composite prosthesis according to claim 14 wherein the biocompatible coating is a hydratable polymer.

21. The composite prosthesis according to claim 14 wherein the mesh is a multifilament mesh.

22. The composite prosthesis according to claim 14 wherein the mesh is a monofilament mesh.

23. The composite prosthesis according to claim 14 wherein the mesh is a polypropylene mesh.

* * * * *